(12) United States Patent
Meredith

(10) Patent No.: US 11,603,436 B2
(45) Date of Patent: Mar. 14, 2023

(54) AROMATIC-BASED POLYETHERAMINE ALKOXYLATES

(71) Applicant: Huntsman Petrochemical LLC, The Woodlands, TX (US)

(72) Inventor: Matthew T. Meredith, The Woodlands, TX (US)

(73) Assignee: HUNTSMAN Petrochemical LLC, The Woodlands, TX (US)

( * ) Notice: Subject to any disclaimer, the term of this patent is extended or adjusted under 35 U.S.C. 154(b) by 270 days.

(21) Appl. No.: 16/765,949

(22) PCT Filed: Oct. 30, 2018

(86) PCT No.: PCT/US2018/058077
§ 371 (c)(1),
(2) Date: May 21, 2020

(87) PCT Pub. No.: WO2019/125603
PCT Pub. Date: Jun. 27, 2019

(65) Prior Publication Data
US 2020/0332072 A1    Oct. 22, 2020

Related U.S. Application Data

(60) Provisional application No. 62/608,003, filed on Dec. 20, 2017.

(51) Int. Cl.
| | |
|---|---|
| *C11D 3/30* | (2006.01) |
| *C11D 3/386* | (2006.01) |
| *C08G 81/00* | (2006.01) |
| *A01N 25/04* | (2006.01) |
| *A01N 25/30* | (2006.01) |
| *C08G 65/333* | (2006.01) |

(52) U.S. Cl.
CPC ............ *C08G 81/00* (2013.01); *A01N 25/04* (2013.01); *A01N 25/30* (2013.01); *C08G 65/33306* (2013.01); *C08G 2650/58* (2013.01)

(58) Field of Classification Search
None
See application file for complete search history.

(56) References Cited

U.S. PATENT DOCUMENTS

| | | |
|---|---|---|
| 3,152,998 A | 10/1964 | Moss |
| 3,654,370 A | 4/1972 | Yeakey |
| 4,014,933 A | 3/1977 | Boettger et al. |
| 4,152,353 A | 5/1979 | Habermann |
| 4,766,245 A | 8/1988 | Larkin et al. |
| 4,891,160 A | 1/1990 | Vander Meer |
| 5,565,145 A | 10/1996 | Watson et al. |
| 2009/0149369 A1 | 6/2009 | Tanner et al. |
| 2017/0240692 A1* | 8/2017 | Roland ............... C08G 59/50 |

FOREIGN PATENT DOCUMENTS

| | | |
|---|---|---|
| CN | 1187105 A | 7/1998 |
| CN | 101511175 A | 8/2009 |
| CN | 105860053 A | 8/2016 |
| JP | 2015-502379 A | 1/2015 |
| WO | 1997/023546 | 7/1997 |
| WO | 2005/028457 A | 3/2005 |

OTHER PUBLICATIONS

PubChem CID 11701916 (Create Date Oct. 26, 2006 (Oct. 26, 2006) Date Assessed Feb. 2-19, 2001 (Feb. 1, 2019); p. 3, compound listed) (Year: 2006).*
"PubChem CID 11701916" Create Date: Oct. 26, 2006 (Oct. 26, 2006 Date Accessed: Feb. 1, 2019 (Jan. 2, 2019); p. 3, compound listed.
International Search Report and Written Opinion received in corresponding PCT Application No. PCT/US2018/058077 completed Feb. 1, 2019 and dated Feb. 15, 2019.
Japan office action dated Oct. 26, 2022 for JP Corresponding Application No. 2020-534604.

* cited by examiner

*Primary Examiner* — Brian Gulledge
(74) *Attorney, Agent, or Firm* — Huntsman Petrochemical LLC; Aleece Hayes

(57) ABSTRACT

The present disclosure provides a polyetheramine alkoxylate compound containing aromatic groups in the hydrophobe allowing the compound to exhibit unique functionality, high performance and low cost, but without the toxicity and/or skin and eye irritation problems associated with conventional polyetheramine compounds.

12 Claims, 1 Drawing Sheet

AROMATIC-BASED POLYETHERAMINE ALKOXYLATES

CROSS REFERENCE TO RELATED APPLICATIONS

This application claims priority to U.S. Provisional Patent Application Ser. No. 62/608,003, filed on Dec. 20, 2017, the entire contents of which are hereby expressly incorporated herein by reference.

FIELD

The present disclosure generally relates to an aromatic-based polyetheramine alkoxylate compound derived from phenylmethanol, diphenylmethanol or triphenylmethanol (each of which may be optionally alkylated) and methods for preparing such compounds. The polyetheramine alkoxylate compound of the present disclosure may be used in a variety of applications including, but not limited to, cleaning, fabric treatment, hair conditioning, fuel additive, oil field, agricultural, personal care and anti-microbial formulations, curable resin compositions, metal-working fluids and in the manufacture of polyurethane foam.

BACKGROUND

Polyetheramine compounds and processes for making such compounds are well known. In general, the process entails: the alkoxylation of an initiator alcohol by the addition of an alkylene oxide (for example, ethylene oxide, propylene oxide or butylene oxide) to form a polyoxyalkylene polyol having various functionalities; and, subjecting the polyoxyalkylene polyol to reductive amination at high temperatures and pressures to produce the polyetheramine.

Various initiator alcohols can be used to derive the polyetheramine compound. For example, one class of initiator alcohols includes fatty alcohols where the fatty chains are principally linear and saturated $C_{14}$-$C_{18}$ groups which are alkoxylated and aminated to form fatty amine alkoxylates.

Because of their unique functionality, high performance and low cost, alcohols containing aromatic groups may also be used as an initiator alcohol. As one skilled in the art is well aware, aromatic alcohols contain a hydroxyl moiety bonded indirectly to an aromatic hydrocarbon group, in contrast to the phenols which contain a hydroxyl group bonded directly to an aromatic carbon. Alkylphenols are one class of such alcohols containing aromatic groups which have achieved wide acceptance in the art, especially with respect to alkoxylates. Another versatile well known class of initiator alcohols containing aromatic groups includes polyarylphenol alcohols, and in particular tristyrylphenol.

Unfortunately, each of the above exhibit undesirable properties, such as toxicity and/or environmental persistence problems. For instance, while fatty alcohols are generally non-toxic, the subsequently produced fatty amine alkoxylates, such as ethoxylated tallow amines, are known to cause eye and skin irritation and have aquatic toxicity. In addition, the use of alkylphenols and tristryphenols has become disfavored due to the fact that alkylphenols are now known to be endocrine disruptors while alkylphenols and tristryphenols are known to be persistent environmental pollutants (see, for example, Soto, A. M. et al. *Environ. Health Persp.* 1991, 92, 167; Environmental risk evaluation report: Styrenated phenol-ISBN 978-1-84911-162-1, 2009).

Accordingly, it would be desirable to identify, develop and employ alternative polyetheramine alkoxylate compounds which can be derived from aromatic alcohols that provide at least similar performance to state of the art polyetheramine alkoxylates, demonstrate reduced eye/skin irritation and toxicity and are also environmentally friendly.

SUMMARY

According to one embodiment, the present disclosure provides a polyetheramine alkoxylate compound having the formula (1)

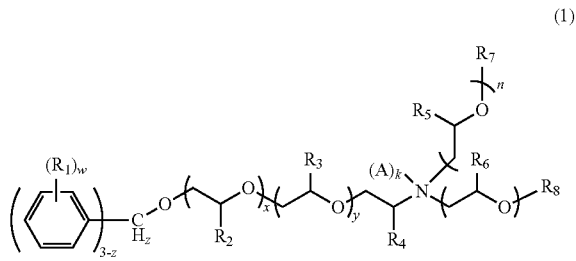

(1)

where each $R_1$ is independently hydrogen or an alkyl group; each $R_2$, $R_3$, $R_4$, $R_5$ and $R_6$ are independently hydrogen, methyl or ethyl; $R_7$ and $R_8$ are independently hydrogen, $SO_3M$, COOM or $PO_3M_2$; M is hydrogen, a water-soluble cation, a monovalent metal or a polyvalent metal cation; A is methyl, ethyl, oxygen or $CH_2COO$; w is an integer from 0 to 3; z is an integer from 0 to 2; x is an integer from 0 to 100; y is an integer from 0 to 100; m is an integer from 0 to 50; n is an integer from 0 to 50; k is 0 or 1; and wherein x+y=1 to 100. In another embodiment, m+n=1 to 50.

In a further embodiment, there is provided a method of making the polyetheramine alkoxylate compound of formula (1) by reacting phenylmethanol (optionally alkylated), diphenylmethanol (optionally alkylated) or triphenylmethanol (optionally alkylated) or a mixture thereof with an alkylene oxide or a polyalkylene glycol in the presence of an acid catalyst or base catalyst to form a precursor polyol, aminating the precursor polyol to form a polyetheramine and reacting the polyetheramine with an alkylene oxide to form the aromatic-based polyetheramine alkoxylate compound. In further embodiments, the polyetheramine alkoxylate compound may optionally be quaternized or oxidized, in still further embodiments, the polyetheramine alkoxylate may optionally be further reacted with an acid moiety and neutralized with a source of alkali metal, alkaline earth metal, amine or ammonia.

In still another embodiment, there is provided uses of the polyetheramine alkoxylate compounds of the present disclosure, such as in performance chemical formulations or personal care formulations.

DETAILED DESCRIPTION

Figure 1:
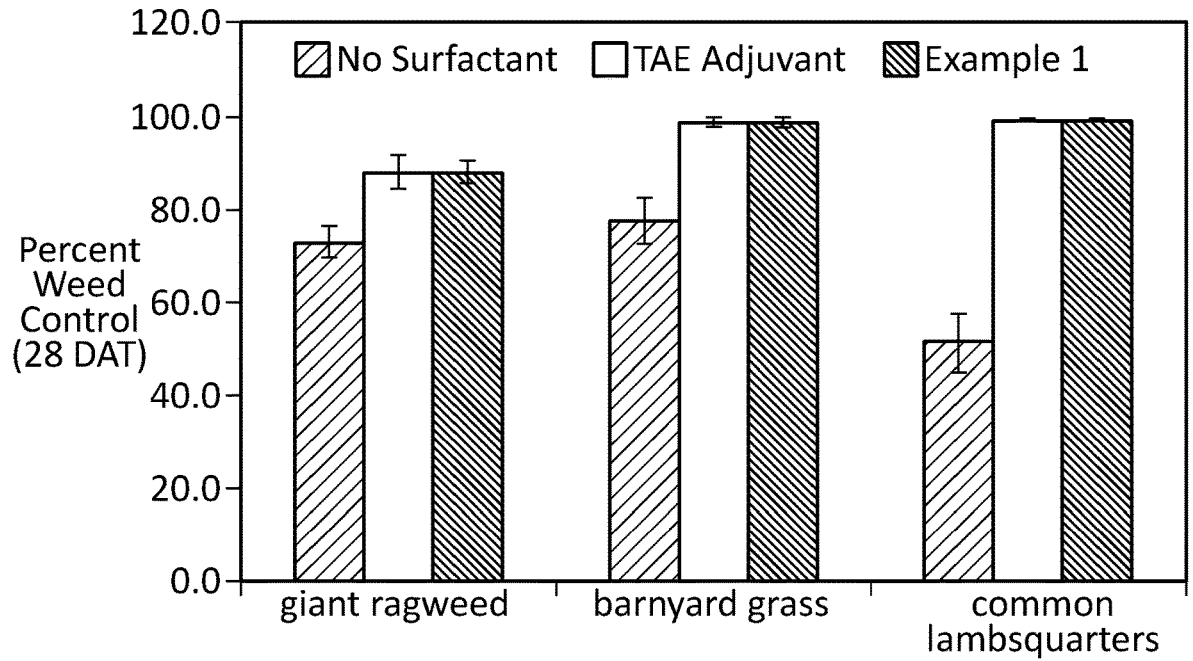
FIGS. 1 and 2 depict the weed-killing efficacy of glyphosate when compounds of the present disclosure and a tallow amine ethoxylate are used as adjuvants.

The following terms shall have the following meanings.

If appearing herein, the term "comprising" and derivatives thereof are not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, except those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical objects of the article. By way of example, "an alkylene oxide" means one alkylene oxide or more than one alkylene oxide. The phrases "in one embodiment", "according to one embodiment" and the like generally mean the particular feature, structure, or characteristic following the phrase is included in at least one embodiment of the present disclosure, and may be included in more than one embodiment of the present disclosure. Importantly, such phrases do not necessarily refer to the same embodiment. If the specification states a component or feature "may", "can", "could", or "might" be included or have a characteristic, that particular component or feature is not required to be included or have the characteristic.

The term "aliphatic" or "aliphatic group," as used herein, denotes a hydrocarbon moiety that may be straight-chained (i.e. unbranched), branched, or cyclic (including fused, bridging, and spirofused polycyclic) and may be completely saturated or may contain one or more units of unsaturation, but which is not aromatic. Unless otherwise specified, aliphatic groups can have from 1 to 20 carbon atoms.

The term "alkyl" is inclusive of both straight chain and branched chain groups and of cyclic groups. Straight chain and branched chain groups may have up to 20 carbon atoms unless otherwise specified. Cyclic groups can be monocyclic or polycyclic, and in some embodiments, can have from 3 to 10 carbon atoms.

The term "alkaryl" means an aryl group substituted with an alkyl group.

The "alkenyl" as used herein is a hydrocarbon group having from 2 to 20 carbon atoms with a structural formula containing at least one carbon-carbon double bond.

The term "alkoxy" means a straight or branched chain hydrocarbon ether group of 10 or less carbon atoms, including methoxy, ethoxy, 2-propoxy, propoxy, butoxy, 3-pentoxy and the like.

The term "alkoxylate" includes pure substances as well as mixtures which are obtained using different alkylene oxides and/or different alcohols.

The term "aromatic" refers to compounds that have unsaturated cyclic hydrocarbons containing one or more rings.

The term "aryl" as used herein is a group that contains any carbon-based aromatic group including, but not limited to, benzene, naphthalene, phenyl, biphenyl, anthracene, and the like, having from 6 to 20 carbon atoms.

The term "carbocyclic" means having or relating to or characterized by a ring composed of 4 to 20 carbon atoms.

The term "cycloalkenyl" means a non-aromatic monocyclic or multicyclic ring system having a single radical and containing a carbon-carbon double bond and having 3 to 10 carbon atoms. Exemplary monocyclic cycloalkenyl rings include cyclopentenyl, cyclohexenyl or cycloheptenyl. An exemplary multicyclic cycloalkenyl ring is norbornenyl.

The term terms "halo," "halogen," or "halide," as used herein can be used interchangeably and refer to F, Cl, Br, or I.

The term "heteroaryl" means a monocyclic or bicyclic radical of 5 to 12 ring atoms having at least one aromatic ring containing one, two, or three ring heteroatoms selected from N, O, and S, the remaining ring atoms being carbon atoms.

The term "heterocyclic" means non-aromatic mono- or bi-cyclic radicals of 3 to 8 ring atoms in which one or two ring atoms are heteroatoms selected from N, O, or $S(O)_n$ (where n is an integer from 0 to 2), the remaining ring atoms being carbon atoms.

The term "hydroxyl" or "hydroxy" as used herein is represented by the formula —OH.

The term "substantially free" means, when used with reference to the substantial absence of a component in a composition, that such a component is not present, or if at all, as an incidental impurity or by-product. In other words, the component does not affect the properties of the composition.

The term "performance chemicals formulations" refers to non-personal care formulations that serve a broad variety of applications, and include non-limiting formulations such as, adhesives, agricultural, biocides, coatings, electronics, household-industrial-institutional (HI&I), inks, membranes, metal working, paper, paints, plastics, printing, plasters, oil field, polyurethane, textile and wood-care formulations.

The term "personal care formulation" refers to such illustrative non-limiting formulations as skin, sun, oil, hair, cosmetic, and preservative formulations, including those to alter the color and appearance of the skin. Potential personal care formulations include, but are not limited to, polymers for increased flexibility in styling, durable styling, and increased humidity resistance for hair, skin, and color cosmetics, sun care water-proof/resistance, wear-resistance, and thermal protecting/enhancing formulations.

The term "fuel additive" means an additive that imparts beneficial properties to fuel and/or an engine and related fuel-handling components.

According to one embodiment, the present disclosure provides a novel polyetheramine alkoxylate compound containing aromatic groups in the hydrophobe which allows the compound to exhibit the unique functionality, high performance and low cost of alkylphenols and tristryphenols, but without the toxicity and/or environmental persistence problems associated with these conventional compounds. In particular, Applicants have surprisingly found that placement of an alkyl spacer between the aromatic moiety and hydroxyl group, in contrast with the direct attachment of the hydroxyl group to the aromatic moiety, maximizes the biodegradation characteristics of the compounds of the present disclosure. Initially, it must be understood that the compounds of the present disclosure are not phenols. That is to say, the indirect attachment of the hydroxyl group to the aromatic moiety of the present compounds eliminates the donation of electrons from the electron-enriched oxygen group to the aromatic ring. Without wishing to be bound by theory, it is believed that this indirect attachment of the hydroxyl group to the aromatic moiety results in the decreased polarization and polarizability of the present compounds, thereby increasing their biodegradability without effecting the performance properties of the inventive compounds. They have surprisingly been found to exhibit performance properties that are at least comparable, or even improved, to those for state of the art compounds, such as fatty amine alkoxylates.

According to one embodiment, the polyetheramine alkoxylate compound is a compound having the general formula (1)

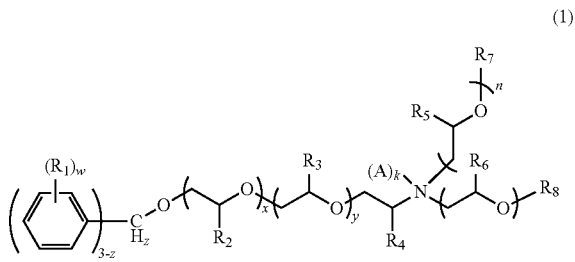

where each $R_1$ is independently hydrogen or an alkyl group; each $R_2$, $R_3$, $R_4$, $R_5$ and $R_6$ are independently hydrogen, methyl or ethyl; $R_7$ and $R_8$ are independently hydrogen, $SO_3M$, COOM or $PO_3M_2$; M is hydrogen, a water-soluble cation, a monovalent metal or a polyvalent metal cation; A is methyl, ethyl, oxygen or $CH_2COO$; w is an integer from 0 to 3; z is 0, 1 or 2; x is an integer from 0 to 100; y is an integer from 0 to 100; m is an integer from 0 to 50; n is an integer from 0 to 50; k is 0 or 1; and wherein x+y=1 to 100. In some embodiments, M may independently be hydrogen, sodium, potassium, magnesium, or calcium.

According to another embodiment, the polyetheramine alkoxylate compound is a compound having the general formula (1)

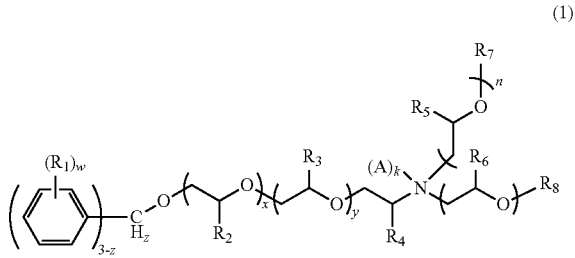

where each $R_1$ is independently hydrogen or an alkyl group; each $R_2$, $R_3$, $R_4$, $R_5$ and $R_6$ are independently hydrogen, methyl or ethyl; $R_7$ and $R_8$ are independently hydrogen, $SO_3M$, COOM or $PO_3M_2$; M is hydrogen, a water-soluble cation, a monovalent metal or a polyvalent metal cation; A is methyl, ethyl, oxygen or $CH_2COO$; w is an integer from 0 to 3; z is 0, 1 or 2; x is an integer from 0 to 50; y is an integer from 0 to 50; m is an integer from 0 to 50; n is an integer from 0 to 50; k is 0 or 1; and wherein x and y x+y=1 to 100 and m+n=1 to 50. In some embodiments, M may independently be hydrogen, sodium, potassium, magnesium, or calcium.

According to one particular embodiment, z is 2 and w is 0 in the compound of formula (1). In yet another embodiment, z is 2, w is 1 and $R_1$ is a $C_4$-$C_{14}$ alkyl group, while in other embodiments $R_1$ is a $C_6$-$C_{12}$ alkyl group or in still other embodiments $R_1$ is a $C_8$-$C_{10}$ alkyl group in the compound of formula (1). In still another embodiment, z is 2, w is 2 and at least one $R_1$ is a $C_4$-$C_{14}$ alkyl group, while in other embodiments at least one $R_1$ is a $C_6$-$C_{12}$ alkyl group or in still other embodiments at least one $R_1$ is a $C_8$-$C_{10}$ alkyl group in the compound of formula (1).

According to another embodiment, z is 1 and w is 0 in the compound of formula (1). In yet another embodiment, z is 1, w is 1 and $R_1$ is a $C_4$-$C_{14}$ alkyl group, while in other embodiments $R_1$ is a $C_6$-$C_{12}$ alkyl group or in still other embodiments $R_1$ is a $C_8$-$C_{10}$ alkyl group in the compound of formula (1). In still another embodiment, z is 1, w is 2 and at least one $R_1$ is a $C_4$-$C_{14}$ alkyl group, while in other embodiments at least one $R_1$ is a $C_6$-$C_{12}$ alkyl group or in still other embodiments at least one $R_1$ is a $C_8$-$C_{10}$ alkyl group in the compound of formula (1).

In still yet another embodiment, in the compound of formula (1), z is 0 and w is 0. In yet another embodiment, in the compound of formula (1), z is 0, w is 1 and $R_1$ is a $C_4$-$C_{14}$ alkyl group, while in other embodiments $R_1$ is a $C_6$-$C_{12}$ alkyl group or in still other embodiments $R_1$ is a $C_8$-$C_{10}$ alkyl group. In still another embodiment, in the compound of formula (1), z is 0, w is 2 and at least one $R_1$ is a $C_4$-$C_{14}$ alkyl group, while in other embodiments at least one $R_1$ is a $C_6$-$C_{12}$ alkyl group or in still other embodiments at least one $R_1$ is a $C_8$-$C_{10}$ alkyl group.

According to another particular embodiment, in the compound of formula (1), x is 0 to 50, y is 0 to 50 and x+y=1 to 50. In still other embodiments, in the compound of formula (1), x is 0 to 20, y is 0 to 20 and x+y=1 to 20, while in further embodiments, x is 0 to 10, y is 0 to 10 and x+y=1 to 10. In still yet another embodiment, in the compound of formula (1), $R_4$ is methyl or ethyl, in some embodiments, methyl and $R_2$ and $R_3$ are chosen such that the x groups and the y groups are random or block groups of ethylene oxide, propylene oxide or butylene oxide. In other embodiments, the oxyalkylene x and y groups may also be mixed randomly or in blocks. In one particular embodiment, in the compound of formula (1), each $R_2$ and $R_3$ independently is hydrogen or methyl and the oxyalkylene groups x and x are arranged in block or random groups of ethylene oxide and propylene oxide.

According to yet another particular embodiment, in the compound of formula (1), m is 0 to 50, n is 0 to 50 and m+n=2 to 50. In still other embodiments, m is 0 to 20, n is 0 to 20 and m+n=2-20, while in other embodiments, m is 0 to 10, n is 0 to 10 and m+n=2 to 10. In still yet another embodiment, in the compound of formula (1), $R_5$ and $R_6$ are chosen such that the m groups and the n groups are random or block groups of ethylene oxide, propylene oxide or butylene oxide. In one particular embodiment, in the compound of formula (1), each $R_5$ and $R_6$ independently is hydrogen or methyl and the oxyalkylene groups m and n are arranged in block or random groups of ethylene oxide and propylene oxide.

In an additional embodiment, in the compound of formula (1), k is 0. In another embodiment, in the compound of formula (1), k is 1 and A is methyl or ethyl. In still another embodiment, in the compound of formula (1), k is 1 and A is O or $CH_2COO$.

According to yet another particular embodiment, in the compound of formula (1), $R_7$ and $R_8$ are hydrogen or methyl. In still another embodiment, in the compound of formula (1), one of $R_7$ or $R_8$ is $SO_3M$ or $PO_3M$ and the other is hydrogen or methyl where M is hydrogen, sodium potassium, magnesium or calcium.

The compound of formula (1) may generally be prepared by converting an initiator alcohol selected from phenylmethanol, diphenylmethanol, triphenylmethanol and a mixture thereof to a precursor polyol, aminating the precursor polyol to form a polyetheramine and alkoxylating the polyetheramine with an alkylene oxide to form the polyetheramine alkoxylate of formula (1).

It has been found that the initiator alcohol may be converted to a precursor polyol by at least two different methods. According to one method, the precursor polyol may be prepared by direct alkoxylation of the initiator alcohol using alkylene oxides, such as ethylene oxide, propylene oxide, butylene oxide and mixtures thereof. Alternatively, the precursor polyol may be prepared by direct condensation of the initiator alcohol with hydroxyl-terminated polyglycol ethers in the presence an acid catalyst. Advantages for this particular method include the avoidance of handling toxic gaseous materials, such as ethylene oxide, and performance of the reaction at atmospheric pressure and relatively low temperatures, such as 50°–150° C. or in some embodiments 80°–120° C. As one skilled in the art is aware, when the initiator alcohol is converted to a precursor polyol as above, a mixture of precursor polyols are generally formed.

Thus, in one embodiment the precursor polyol prepared by the polyaddition of alkylene oxide(s) to the initiator alcohol. In another embodiment, the precursor polyol is prepared by reacting (condensing) the initiator alcohol with methyl-terminated polyethylene glycol (m PEG), polyethylene glycol (PEG) or other polyalkylene glycols (PAG) in the presence of an acid catalyst. In still other embodiments, diphenylmethanol used in the reaction above may be obtained from benzophenone which has been hydrogenated in the presence of a hydrogenation catalyst.

In one particular embodiment where the precursor polyol is prepared by alkoxylation, such alkoxylation can be catalyzed by an alkoxylation catalyst including those well known to those skilled in the art. Examples include, but are not limited to, strong bases, such as alkali metal hydroxides and alkaline earth metal hydroxides, Brønsted acids or Lewis acids such as A1013, BF3, and the like. Catalysts such as hydrotalcite or DMC may be also used when alkoxylates with a narrow distribution are desired.

Additionally, the alkoxylation may be carried out at temperatures in a range of about 80°-250° C., such as about 100°-220° C. The pressure may be between ambient pressure and 600 bar. If desired, the alkylene oxide may comprise a mixture of inert gas, for example approximately 5% to 60%.

As discussed above, the ethylene oxide, propylene oxide, butylene oxide units may be arranged within the compound of formula (1) in any way. Thus, for example, the structural units x and y may be arranged at random or in blocks. The alkoxylation can therefore be carried out using only a single type of alkylene oxide, as well as a mixture of alkylene oxides. If, for example, a mixture of two or more different alkylene oxides is introduced into the reaction mixture, this generally leads, if the reactivity of the alkylene oxides is essentially comparable, to random polyether chains in which the constituents of the mixture are not present in any particular order. However, if the different alkylene oxides are fed into the reaction mixture in succession, i.e. a further alkylene oxide intended for the reaction is only fed in when that previously fed in has reacted completely, polyether segments are made up of blocks.

The degree of alkoxylation, i.e. the mean chain length of the polyether chains of aromatic alkoxylates according to the disclosure and their composition (in other words, the values of x and y) can be controlled by the ratio of the molar amounts of the initiator alcohol to alkylene oxide(s) employed in their preparation, and by the reaction conditions. On the one hand, the precursor polyol may comprise at least or more than approximately 4, in some embodiments at least or more than approximately 10, in other particular embodiments at least or more than approximately 30, and still other embodiments at least or more than approximately 50 alkylene oxide units. On the other hand, the precursor polyol may comprise not more than or less than approximately 100 or 70 or 40 or 10 alkylene oxide units.

The precursor polyol is then used as a feedstock in a reductive amination step. In some instances, prior to reductive amination, the precursor polyol is neutralized with acid or chemical adsorbent, such as for example, oxalic acid or magnesium silicate, and filtered for the removal of insoluble materials. The precursor polyol is charged to a reductive amination zone where it is brought into contact with a reductive amination catalyst, sometimes referred to as a hydrogenation-dehydrogenation catalyst, and reductively aminated in the presence of ammonia and hydrogen under reductive amination conditions. Reductive amination conditions may include, for example, a temperature within the range of about 150° C. to about 275° C. and a pressure within the range of about 500 psi to about 5000 psi with temperatures within the range of about 180° C. to about 220° C. and pressures within the range of about 1500 psi to about 2500 psi being used in many embodiments.

Any suitable hydrogenation catalyst may be used, such as those described in U.S. Pat. No. 3,654,370, the contents of which are incorporated herein by reference. In some embodiments, the hydrogenation catalyst may comprise one or more of the metals of group VIIIB of the Periodic Table, such as iron, cobalt, nickel, ruthenium, rhodium, palladium or platinum, mixed with one or more metals of group VIB of the Periodic Table such as chromium, molybdenum or tungsten. A promoter from group IB of the Periodic Table, such as copper, may also be included. As an example, a catalyst may be used comprising from about 60 mole percent to about 85 mole percent of nickel, about 14 mole percent to about 37 mole percent of copper and about 1 mole percent to about 5 mole percent of chromium (as chromia), such as a catalyst of the type disclosed in U.S. Pat. No. 3,152,998. As another example, a catalyst of the type disclosed in U.S. Pat. No. 4,014,933 may be used containing from about 70% by weight to about 95% by weight of a mixture of cobalt and nickel and from about 5% by weight to about 30% by weight of iron. As another example, a catalyst of the type disclosed in U.S. Pat. No. 4,152,353 may be used, comprising nickel, copper and a third component which may be iron, zinc, zirconium or a mixture thereof, for example, a catalyst containing from about 20% by weight to about 49% by weight of nickel, about 36% by weight to about 79% by weight of copper and about 1% by weight to about 15% by weight of iron, zinc, zirconium or a mixture thereof. As still another example, a catalyst of the type described in U.S. Pat. No. 4,766,245 may be used comprising about 60% by weight to about 75% by weight of nickel and about 25% by weight to about 40% by weight of aluminum.

Thus, precursor polyol is aminated to form a compound having the general formula (2)

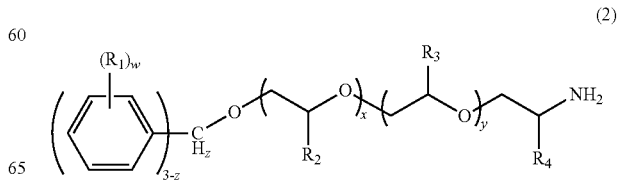

where z, w, x, y, $R_2$, $R_3$ and $R_4$ are defined as above.

The compound of formula (2) may find use in a variety of applications, such as a surfactant for personal care and performance chemical formulations, as a curing agent for a curable resin or as a reactant in the production of polyurea or polyurethane.

The compound of formula (2) can then be alkoxylated to form the compound of formula (1) (i.e. where m+n=at least 1 to 50). The polyetheramine alkoxylate compounds of (1) can be prepared by known standard methods for alkoxylating amines (see, for e.g. U.S. Pat. Nos. 4,891,160 and 5,565,145 and WO 1997/023546, the contents of which are hereby incorporated by reference) and as described above with respect to the initiator alcohol. In general, the compound of formula (2) is reacted with an alkylene oxide, optionally in the presence of an alkoxylation catalyst, at a temperature from about 40° C. to about 150° C. The amount of alkylene oxide used may range from about 0.5 to about 2 moles per mole of the compound of formula (2). As described above, the structural unit m and n may also be arranged at random or in blocks based on the addition of the alkylene oxide to the reaction mixture.

In further embodiments, the polyetheramine alkoxylate compound of formula (1) may be converted to a sulfonate, carboxylate or phosphate by conventional techniques, such as by further reaction with an acidic moiety and optionally neutralized with a source of alkali metal or alkaline earth metal.

In still further embodiments, the polyetheramine alkoxylate compound of formula (1) may be reacted with a halo-substituted carboxylic acid, such as monochloroacetate, to form a betaine, while in other embodiments the compound of formula (1) may be reacted with an oxidizing agent, such as hydrogen peroxide or benzoyl peroxide, to form an oxide.

As described above, the compound of formula (1) may find use in a variety of compositions. Thus, in one embodiment, there is provided a composition comprising a polyetheramine alkoxylate compound having the formula (1)

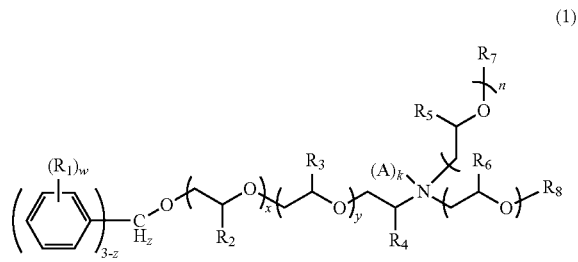

(1)

where each $R_1$ is independently hydrogen or an alkyl group; each $R_2$, $R_3$, $R_4$, $R_5$ and $R_6$ are independently hydrogen, methyl or ethyl; $R_7$ and $R_8$ are independently hydrogen, $SO_3M$, COOM or $PO_3M_2$; M is hydrogen, a water-soluble cation, a monovalent metal or a polyvalent metal cation; A is methyl, ethyl, oxygen or $CH_2COO$; w is an integer from 0 to 3; z is 0, 1 or 2; x is an integer from 0 to 100; y is an integer from 0 to 100; m is an integer from 0 to 50; n is an integer from 0 to 50; k is 0 or 1; and wherein x+y=1 to 100 and m+n=1 to 50.

In still another embodiment, the composition may further include a solvent. According to one embodiment the solvent is water, and in some embodiments, de-ionized water. In other embodiments a different solvent may be used in addition to or in place of water. Examples of such solvents include, but are not limited to, hydrocarbons (e.g. pentane or hexane), halocarbons (e.g. Freon 113), ethers (e.g. ethylether ($Et_2O$), tetrahydrofuran ("THF") or diglyme (diethyleneglycol dimethyl ether)), nitriles (e.g. $CH_3CN$), or aromatic compounds (e.g. benzotrifluoride). Still further exemplary solvents include lactates, pyruvates, and diols. Solvents can also include, but are not limited to, acetone, 1,4-dioxane, 1,3-dioxolane, ethyl acetate, cyclohexanone, acetone, 1-methyl-2-pyrodidianone (NMP), and methyl ethyl ketone. Other solvents, include dimethylformamide, dimethylacetamide, N-methyl pyrrolidone, ethylene carbonate, propylene carbonate, glycerol and derivatives, naphthalene and substituted versions, acetic acid anhydride, propionic acid and propionic acid anhydride, dimethyl sulfone, benzophenone, diphenyl sulfone, phenol, m-cresol, dimethyl sulfoxide, diphenyl ether, terphenyl, and the like. Still further solvents include propylene glycol propyl ether (PGPE), 3-heptanol, 2-methyl-1-pentanol, 5-methyl-2-hexanol, 3-hexanol, 2-heptanol, 2-hexanol, 2,3-dimethyl-3-pentanol, propylene glycol methyl ether acetate (PGMEA), ethylene glycol, isopropyl alcohol (IPA), n-butyl ether, propylene glycol n-butyl ether (PGBE), 1-butoxy-2-propanol, 2-methyl-3-pentanol, 2-methoxyethyl acetate, 2-butoxyethanol, 2-ethoxyethyl acetoacetate, 1-pentanol, and propylene glycol methyl ether. The solvents enumerated above may be used alone or in combination.

In another embodiment, the composition may optionally contain a dispersant. In certain embodiments, the dispersant may be an ionic or a nonionic compound. The ionic or nonionic compound may further comprise a copolymer, an oligomer, or a surfactant other than the polyetheramine alkoxylate compound of formula (1), alone or in combination. The term copolymer, as used herein, relates to a polymer compound consisting of more than one polymeric compound such as block, star, dendrimer or grafted copolymers. Examples of a nonionic copolymer dispersant include polymeric compounds such as the tri-block EO-PO-EO co-polymers PLURONIC® L121, L123, L31, L81, L101 and P123 products. The term oligomer, as used herein, relates to a polymer compound consisting of only a few monomer units. Examples of ionic oligomer dispersants include SMA® 1440 and 2625 products.

Surfactants useful in the composition of the present disclosure are well known and include anionic, nonionic, cationic and amphoteric compounds. Combinations of more than one such compounds may be used in the composition.

Anionic surfactant compounds which may be used include, but are not limited to, alkyl sulfates, alkyl benzene sulfonates, α-olefin sulfonates, alkyl taurates, alkyl sacrosinates, alkyl diphenyloxide disulfonates, alkyl naphthalene sulfonates, alkyl ether sulfates, alkyl ether sulfonates, sulfosuccinates, and other anionic surfactants as known for use in, for example, performance chemical formulations, including linear $C_{8-16}$ alkyl sulfates, $C_{8-16}$ alkyl sulfonates, $C_{8-16}$ alkyl benzene sulfonates and $C_{8-16}$ alkyl diphenyloxide disulfonates, decyl sulfophenoxy benzene/oxybis decyl benzene sulfonic acid disodium salt, and sodium octane sulfonate, sodium dodecyl sulfonate, sodium lauryl sulfate, and combinations of the foregoing. These surfactants are typically available as the alkali metal, alkaline earth and ammonium salts thereof.

Nonionic surfactant compounds which may be used include, but are not limited to, alkoxylates, N-substituted fatty acid amides, amine oxides, esters, sugar-based surfactants, polymeric surfactants, and mixtures thereof. Examples of alkoxylates are compounds such as non-aromatic alcohols, amines, amides, fatty acids or fatty acid esters which have been alkoxylated with 1 to 50 equivalents. Ethylene oxide and/or propylene oxide may be employed for the alkoxylation, usually ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters. Examples of polymeric surfactants are homo- or copolymers of vinylpyrrolidone, vinylalcohols, or vinylacetate.

Cationic surfactant compounds may also be used including quaternary surfactants, for example quaternary ammonium compounds with one or two hydrophobic groups, or salts of long-chain primary amines.

Amphoteric surfactant compounds which may be used include, but are not limited to, betaines, alkyl imidazolines, cocoamphopropionates, disodium cocoamphodipropionate (also known as cocoimidazoline carboxylate), or combinations thereof.

Other known additives, besides those described above, may optionally be added to the composition depending upon the application. These additives may include, but are not limited to, colorants, enzymes, wetting agents, antifoaming agents, buffering agents, pH adjusting agents, thickening agents, emulsifiers, anti-streaking agents, builders, chelating or sequestering agents, hydrotopes, anti-microbial agents, perfumes, herbicides, pesticides, fungicides, anti-oxidants, anti-wear additives, friction modifiers, viscosity index improvers, pour point depressants, corrosion inhibitors, solid carriers or fillers, protective colloids, adhesion agents, humectants, repellents, attractants, feeding stimulants, compatibilizers, bactericides, anti-freezing agents, crystallization inhibitors, tackifiers, binders, preservatives, clarifiers, fertilizers, UV stabilizers, salts, weighting agents, gravel particulates, gases, crosslinkers, thermodynamic hydrate inhibitors, kinetic hydrate inhibitors, clay stabilizing agents and mixtures thereof.

According to another embodiment, there is provided a composition comprising the compound of formula (1) above and wherein the composition is substantially free of tallow amine alkoxylates, alkylphenol alkoxylates and polyarylphenol alkoxylates.

In yet another embodiment, there is provided a packaged product comprising: a) a container having at least an outlet; and b) a composition comprising the compound of formula (1).

According to one embodiment, the packaged product of the present disclosure comprises a container having a closure means, such as a lid, cover, cap, or plug to seal the container. In another embodiment, the sealed container also has a nozzle or pour spout. The sealed container may have the shape of a cylinder, oval, round, rectangle, canister, tub, square or jug and contains the composition of the present disclosure.

The container may be made from any material, such as steel, glass, aluminum, cardboard, tin-plate, plastics including, but not limited to, high density polyethylene (HDPE), polypropylene (PP), polyvinyl chloride (PVC), polyethylene terephthalate (PET), oriented polypropylene (OPP), polyethylene (PE) or polyamide and including mixtures, laminates or other combinations of these.

In another embodiment, a concentrated composition comprising the compound of formula (1) is provided that may be further diluted in water and/or other solvents to form an aqueous solution. A concentrated composition of the present disclosure, or "concentrate" allows one to dilute the concentrate to the desired strength and pH. A concentrate also permits longer shelf life and easier shipping and storage. Thus, in one embodiment there is provided a concentrate composition containing the compound of the formula (1) of the present disclosure and water and/or other solvent and optionally one or more additives described above. For the concentrate, the amount of water (and in some embodiments, de-ionized water) and/or solvent may, for instance, be from about 0.5 to about 50% by weight, based on the total weight of the concentrate. Accordingly, the amount of the compound of formula (1) (and optional additives if present) contained in the concentrate may range from about 50% by weight up to 99.5% by weight, based on the total weight of the concentrate. As noted above, the concentrate may be further diluted with water, and in some embodiments, de-ionized water, and/or solvent to form the aqueous solution.

The composition including the polyetheramine alkoxylate compound of formula (1) of the present disclosure may be used in a variety of applications and formulations, including, but not limited to, performance chemical formulations and personal care formulations.

Thus, in one embodiment there is provided a performance chemical formulation containing the composition comprising the compound of formula (1) wherein the compound of formula (1) is present in the performance chemical formulation in an amount ranging from about 0.01% by weight to about 40% by weight, based on the total weight of the performance chemical formulation. In another embodiment, there is provided a performance chemical formulation containing the composition comprising the compound of formula (1) wherein the compound of formula (1) is present in the performance chemical formulation in an amount ranging from about 0.1% by weight to about 30% by weight, based on the total weight of the performance chemical formulation. In still another embodiment, there is provided a performance chemical formulation containing the composition comprising the compound of formula (1) wherein the compound of formula (1) is present in the performance chemical formulation in an amount ranging from about 0.5% by weight to about 20% by weight, based on the total weight of the performance chemical formulation. In yet still another embodiment, there is provided a performance chemical formulation containing the composition comprising the compound of formula (1) wherein the compound of formula (1) is present in the performance chemical formulation in an amount ranging from about 1% by weight to about 10% by weight, based on the total weight of the performance chemical formulation.

Accordingly, in still another embodiment there is provided a personal care formulation containing the composition comprising the compound of formula (1) wherein the compound of formula (1) is present in the personal care formulation in an amount ranging from about 0.01% by weight to about 40% by weight, based on the total weight of the performance chemical formulation. In another embodiment, there is provided a performance chemical formulation containing the composition comprising the compound of formula (1) wherein the compound of formula (1) is present in the personal care formulation in an amount ranging from about 0.1% by weight to about 30% by weight, based on the total weight of the personal care formulation. In still another embodiment, there is provided a personal care formulation containing the composition comprising the compound of formula (1) wherein the compound of formula (1) is present in the personal care formulation in an amount ranging from about 0.5% by weight to about 20% by weight, based on the total weight of the personal care formulation. In yet still another embodiment, there is provided a personal care formulation containing the composition comprising the compound of formula (1) wherein the compound of formula (1) is present in the personal care formulation in an amount ranging from about 1% by weight to about 10% by weight, based on the total weight of the personal care formulation.

In one particular embodiment, there is provided an agrochemical emuslfiable concentrate containing an agrochemical active component, a solvent and the composition comprising the compound of formula (1).

Examples of agrochemical active components include, but are not limited to, a pesticide, fungicide, herbicide, insecticide, algicide, molluscicide, miticide, rodenticide, growth regulator or insect repellant. In one particular embodiment, the agrochemical active component includes an insecticide, such as Malathion, Chlorpyrifos, Cypermethrin and Chloropicrin, a herbicide, such as Trifluralin, 2,4-D Ester, MCPA Isooctylester, Metolachlor, Acetochlor, Triclopyr and Roundup®, or a fungicide, such as Mefenoxam and Etridiazole The agrochemical active component or components may be present in the agrochemical emulsifiable concentrate in an amount of at least about 5% w/w, or at least about 7.5% w/w, or at least about 10% w/w, where w/w means the weight of the agrochemical active component present in the agrochemical emulsifiable concentrate over the total weight of the agrochemical emulsifiable concentrate. In another embodiment, the agrochemical active component or components may be present in the agrochemical emulsifiable concentrate in an amount of less than about 80% w/w, or less than about 70% w/w, or less than about 60% w/w, or even less than about 50% w/w, where w/w means the weight of the agrochemical active component present in the agrochemical emulsifiable concentrate over the total weight of the agrochemical emulsifiable concentrate.

Examples of solvents include, but are not limited to, those described above. In another embodiment, the solvent may be a hydrocarbon, ether, phenol, glycol, lactone, chlorinated hydrocarbon, aromatic hydrocarbon nitrated hydrocarbon, dibasic ester, mono-ester such as ethyl acetate, butyl acetate, ethyl-3-ethoxy-propionate, propylene glycol methyl ether acetate, propylene glycol butyl ether acetate, dipropylene glycol methyl ether acetate, dipropylene glycol butyl ether acetate and a cyclic ester such as butyrolactone, organic sulfur-containing compounds dimethylsulfoxide (DMSO) and sulfolane, methyl ethyl ketone (MEK), 5-methyl-2-hexanone (MIAK), methyl isobutyl ketone and methyl isoamylbutone, a glycol ether such as propylene glycol methyl ether (PM), dipropylene glycol methyl ether (DPM), or dipropylene glycol n-butyl ether (DPNB), ethylene glycol butyl ether (EB) and dipropylene glycol butyl ether (DB), an alcohol such as methanol, ethanol, propanol, butanol, benzyl alcohol, an amide and mixtures thereof. In some embodiments, the solvent may be present in the agrochemical emulsifiable concentrate in an amount of at least 10% w/w, or at least about 15% w/w, or even at least about 20% w/w, where w/w means the weight of the solvent present in the agrochemical emulsifiable concentrate over the total weight of the agrochemical emulsifiable concentrate. In other embodiments, the solvent may be present in the agrochemical emulsifiable concentrate in an amount of less than about 80% w/w, or less than about 70% w/w or even less than about 60% w/w, where w/w means the weight of the solvent present in the agrochemical emulsifiable concentrate over the total weight of the agrochemical emulsifiable concentrate.

In another embodiment, the composition comprising the compound of formula (1) may be present in the agrochemical emulsifiable concentrate in an amount of at least 1% w/w, or at least 5% w/w, or at least 7.5% w/w, where w/w means the weight of the composition comprising the compound of formula (1) present in the agrochemical emulsifiable concentrate over the total weight of the agrochemical emulsifiable concentrate. In another embodiment, the composition comprising the compound of formula (1) may be present in the agrochemical emulsifiable concentrate in an amount of less than about 20% w/w, or less than about 15% w/w, or less than about 10% w/w, where w/w means the weight of the composition comprising the compound of formula (1) present in the agrochemical emulsifiable concentrate over the total weight of the agrochemical emulsifiable concentrate. In another embodiment, the composition comprising the compound of formula (1) may be present in the agrochemical emulsifiable concentrate in an amount ranging from about 1% w/w to about 20% w/w, or from about 2% w/w to about 15% w/w, or from about 5% w/w to about 10% w/w, where w/w means the weight of the composition comprising the compound of formula (1) present in the agrochemical emulsifiable concentrate over the total weight of the agrochemical emulsifiable concentrate.

The agrochemical emulsifiable concentrate may optionally comprise one or more additives described above in an amount up to about 20% w/w, where w/w means the weight of the additives present in the agrochemical emulsifiable concentrate over the total weight of the agrochemical emulsifiable concentrate. In one particular embodiment, the additives may be chosen from crystallization inhibitors, emulsifiers, surfactants other than the compound of formula (1), suspending agents, dyes, anti-oxidants, foaming agents, light absorbers, mixing aids, anti-foams, complexing agents, neutralizing or pH-modifying substances and buffers, corrosion-inhibitors, fragrances, wetting agents, absorption improvers, micronutrients, plasticizers, glidants, lubricants, dispersants, anti-freezes, and/or microbicides.

In another particular embodiment, there is provided an agrochemical suspension concentrate comprising an agrochemical active component, water and the composition comprising the compound of formula (1).

In one embodiment, the agrochemical suspension concentrate may comprise at least about 1% w/w, or at least about 2% w/w, or even at least about 5% w/w, of the agrochemical active component or components, where w/w means the weight of the agrochemical active component or components present in the agrochemical suspension concentrate over the total weight of the agrochemical suspension concentrate. In another embodiment, the agrochemical suspension concentrate may comprise less than about 70% w/w, or less than about 60% w/w, less than about 50% by weight, or less than about 40% by weight of the agrochemical active component or components, where w/w means the weight of the agrochemical active component or components present in the agrochemical suspension concentrate over the total weight of the agrochemical suspension concentrate.

In another embodiment, the agrochemical suspension concentrate may contain at least about 10% w/w of water, or at least about 20% w/w, or even at least about 40% w/w, of water, where w/w means the weight of water present in the agrochemical suspension concentrate over the total weight of the agrochemical suspension concentrate. In another embodiment, the agricultural suspension concentrate may comprise less than about 90% w/w of water, or less than about 80% w/w, or even less than about 75% w/w of water, where w/w means the weight of water present in the agrochemical suspension concentrate over the total weight of the agrochemical suspension concentrate.

In yet another embodiment, the composition comprising the compound of formula (1) may be present in the agrochemical suspension concentrate in an amount of at least 0.5% w/w, or at least 1% w/w, or at least 2.5% w/w, where w/w means the weight of the composition comprising the compound of formula (1) present in the agrochemical suspension concentrate over the total weight of the agrochemical suspension concentrate. In another embodiment, the composition comprising the compound of formula (1) may be present in the agrochemical suspension concentrate in an amount of less than about 10% w/w, or less than about 7.5% w/w, or less than about 5% w/w, where w/w means the weight of the composition comprising the compound of formula (1) present in the agrochemical suspension concentrate over the total weight of the agrochemical suspension concentrate. In another embodiment, the composition comprising the compound of formula (1) may be present in the agrochemical suspension concentrate in an amount ranging from about 0.01% w/w to about 10% w/w, or from about 0.75% w/w to about 7.5% w/w, or from about 1% w/w to about 5% w/w, where w/w means the weight of the composition comprising the compound of formula (1) present in the agrochemical suspension concentrate over the total weight of the agrochemical suspension concentrate.

The agrochemical suspension may optionally contain one or more additives described above in an amount of up to 20% w/w, where w/w means the weight of the additives present in the agrochemical suspension concentrate over the total weight of the agrochemical suspension concentrate.

The composition comprising the compound of formula (1) may also be useful as a fuel additive in a fuel composition. In such embodiments, the fuel composition, which includes the compound of formula (1) and a fuel, is useful in fueling an internal combustion engine or an open flame burner. The fuel composition may also contain one or more additional performance additives. In some embodiments, the fuel composition may include the compound of formula (1) in a minor amount and the fuel in a major amount. In still further embodiments, the compound of formula (1) may be added directly to the fuel composition or it may be added to the fuel composition as a component of a fuel additive concentrate.

Fuels suitable for use are not overly limited. Generally, the fuel is normally liquid at ambient conditions, for example, room temperature (20° C. to 30° C.), or is normally liquid at operating conditions. The fuel can be a hydrocarbon fuel, non-hydrocarbon fuel, or mixture thereof.

The hydrocarbon fuel can be a petroleum distillate, including a gasoline as defined by ASTM specification D4814, or a diesel fuel, as defined by ASTM specification D975. In one embodiment, the fuel is a gasoline, and in another embodiment the fuel is a non-leaded gasoline. In yet another embodiment, the liquid fuel is a diesel fuel. The hydrocarbon fuel can be a hydrocarbon prepared by a gas to liquid process to include for example hydrocarbons prepared by a process such as the Fischer-Tropsch process. In some embodiments, the fuel is a diesel fuel, a biodiesel fuel, or a combination thereof.

The fuel can also include heavier fuel oils, such as number 5 and number 6 fuel oils, which are also referred to as residual fuel oils, heavy fuel oils, and/or furnace fuel oils. Such fuels may be used alone or mixed with other, typically lighter, fuels to form mixtures with lower viscosities. Bunker fuels are also included, which are generally used in marine engines. These types of fuels have high viscosities and may be solids at ambient conditions, but are liquid when heated and supplied to the engine or burner it is fueling.

The non-hydrocarbon fuel can be an oxygen containing composition, often referred to as an oxygenate, which includes alcohols, ethers, ketones, esters of a carboxylic acids, nitroalkanes, or mixtures thereof. Non-hydrocarbon fuels can include methanol, ethanol, methyl t-butyl ether, methyl ethyl ketone, transesterified oils and/or fats from plants and animals such as rapeseed methyl ester and soybean methyl ester, and nitromethane.

Mixtures of hydrocarbon and non-hydrocarbon fuels can include, for example, gasoline and methanol and/or ethanol, diesel fuel and ethanol, and diesel fuel and a transesterified plant oil such as rapeseed methyl ester and other bio-derived fuels. In one embodiment the fuel is an emulsion of water in a hydrocarbon fuel, a non-hydrocarbon fuel, or a mixture thereof.

The fuel is generally present in the fuel composition in a major amount which is generally greater than about 90% by weight, or greater than about 95% by weight, or in other embodiments greater than about 97% by weight, or greater than about 99.5% by weight, or greater than about 99.9% by weight, or even greater than about 99.99% by weight, based on the total weight of the fuel composition.

The composition comprising the compound of formula (1) is generally present in the fuel composition in a minor amount that is generally less than about 10% by weight, or less than about 1% by weight, or less than about 0.5% by weight and even less than about 0.1% by weight (1000 ppmw) (parts per million by weight) based on the total weight of the fuel composition.

In one embodiment, the composition comprising the compound of formula (1) is part of a fuel additive concentrate. Such fuel additive concentrates containing the composition comprising the compound of formula (1) are compositions that may also contain one or more performance additives as well as some amount of fuel, a carrier oil, or a solvent of some type. These fuel additive concentrates can then be added to other compositions as a convenient way to handle and deliver the additives, resulting in the final fuel composition described above. The fuel additive concentrate may, in general, contain the compound of the formula (1) in an amount of about 0.1% by weight to about 80% by weight, or about 0.5% by weight to about 60% by weight, based on the total weight of the fuel additive concentrate.

The additional performance additives can include, but are not limited to: an antioxidant such as a hindered phenol or derivative thereof and/or a diarylamine or derivative thereof; a corrosion inhibitor; and/or a detergent/dispersant additive, such as an additional polyetheramine or nitrogen containing detergent, including but not limited to PIB amine detergents/dispersants, succinimide detergents/dispersants, and other quaternary salt detergents/dispersants including quaternary ammonium imide salts, that is a detergent containing an imide group and a quaternary ammonium salt.

The additional performance additives may also include: a cold flow improver such as an esterified copolymer of maleic anhydride and styrene and/or a copolymer of ethylene and vinyl acetate; a foam inhibitor and/or antifoam agent such as a silicone fluid; a demulsifier such as a polyalkoxylated alcohol; a lubricity agent such as a fatty carboxylic acid; a metal deactivator such as an aromatic triazole or derivative thereof, including but not limited to benzotriazole; and/or a valve seat recession additive such as an alkali metal sulfosuccinate salt.

The additional performance additives may also include a biocide; an antistatic agent, a deicer, a fluidizer such as a mineral oil and/or poly(alpha-olefin) and/or polyether, and a combustion improver such as an octane or cetane improver.

The additional performance additives can each be added directly to the fuel additive concentrate and/or the fuel composition, but they are generally mixed with the fuel additive to form the fuel additive concentrate, which is then mixed with fuel to result in a fuel composition.

The fuel additive concentrate may also include a carrier oil. Examples include those oils of viscosity grade "Solvent Neutral (SN) 500 to 2000", synthetic carrier oils based on olefin polymers having a molecular weight of about 400 to 1800, especially based on polybutene or polyisobutene (hydrogenated or nonhydrogenated), and on polyalphaolefins or internal polyolefins and synthetic carrier oils based on alkoxylated long-chain alcohols or phenols.

The fuel additive concentrate can also comprise a solvent. The solvent provides for a homogeneous and fuel additive concentrate and for facilitating the transfer and handling of the fuel additive concentrate composition. In some embodiments, the solvent is an aliphatic hydrocarbon, aromatic hydrocarbons or a mixture thereof.

Aliphatic hydrocarbons include various naphtha and kerosene boiling point fractions that have a majority of aliphatic components. Aromatic hydrocarbons include benzene, toluene, xylenes and various naphtha and kerosene boiling point fractions that have a majority of aromatic components. In one embodiment, the solvent can be present in the fuel additive concentrate at about 1.0% by weight to about 90% by weight, in another embodiment at about 25% to about 85% by weight, and yet in another embodiment, at about 40% to about 80% by weight, based on the total weight of the fuel additive concentrate.

In still another embodiment, the compound of formula (1) may be used as a curing agent to cure a curable resin. The curable resin may be a benzoxazine resin, an epoxy resin, an episulfide resin, an oxetane resin, a (meth)acrylate resin, a cyanate resin or a mixture thereof. The curable composition may be a one-part curable composition or a multi-part (for e.g. two-part) curable composition where the first part includes the curable resin and the second part includes the compound of formula (1), and the curable composition is formed by combining the first part and second part.

Benzoxazine resins include those compounds having a general structure:

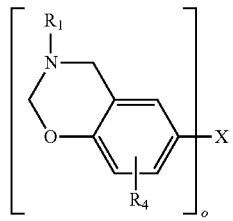

where o is an integer from 1 to 4; each $R_1$ is a substituted or unsubstituted alkyl group, a substituted or unsubstituted alkenyl group, a substituted or unsubstituted aryl group, a substituted or unsubstituted heteroaryl group, a substituted or unsubstituted carbocyclic group, or a substituted or unsubstituted heterocyclic group; each $R_4$ is independently hydrogen, an alkyl group, an alkenyl group, or an aryl group; and X is a direct bond (when o is 2), a substituted or unsubstituted alkyl group, a substituted or unsubstituted aryl group, a substituted or unsubstituted heteroaryl group, S, S=O, O=S=O or C=O. Substituents include, but are not limited to, hydroxy, alkyl, alkoxy, mercapto, heterocyclic, aryl, heteroaryl, halogen, cyano, nitro, nitrone, amino, amido, acyl, oxyacyl, carboxyl, carbamate, sulfonyl, sulfonamide and sulfuryl groups.

The epoxy resin may include, but are not limited to, glycidylated bisphenols (such as bisphenol A or E or F or S diglycidyl ether), glycidylated biphenyls and hydrogenated versions thereof; cycloaliphatic epoxy resins; glycidylated anilines; and glycidylated hydroxyanilines.

Episulfides include, but are not limited to, sulfur analogues of any one or more epoxy resins described above.

The oxetanes may include, but are not limited to, four membered oxygen-containing rings of any one or more epoxy resins described above.

(Meth)acrylate resins may include those compounds represented by the general formula $H_2C=CGCO_2R^6$ where G is hydrogen, halogen or a $C_1$-$C_4$ alkyl group, and $R^6$ is alkyl, alkenyl, cycloalkenyl, alkaryl, or aryl groups, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate and sulfone.

Maleimide resins, which may be in liquid or solid form, include those compounds having the general structure:

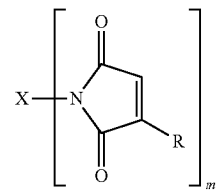

where m is an integer of 1 to 3, X is a branched alkyl or alkylene species having at least 12 carbon atoms and each R is independently hydrogen or a $C_1$-$C_4$ alkyl group.

Cyanate ester resins include those compounds having the general structure $R^{10}$—(O—C≡N)$_d$ where d is an integer of 1 to 10 and $R^{10}$ is a $C_6$-$C_{200}$ aromatic or mixed aromatic-aliphatic hydrocarbon radical containing a member or members selected from the group consisting of oxygen, nitrogen, halogen, sulfur, phosphorus, boron, silicon, hydrogen, and mixtures thereof.

The curable composition may also include customary auxiliary additives such as, but not limited to, a stabilizer, extender, filler, reinforcing agent, pigment, dyestuff, plasticizer, tackifier, rubber, accelerator, diluent or any mixture thereof.

The curable composition will typically include the curable resin in an amount of about 10-90% by weight, or about 20-80% by weight or about 25-70% by weight, or about 30-65% by weight or even about 35-55% by weight, based on the total weight of the curable composition. The curable composition may also include the compound of formula (1) in an amount of about 1-35% by weight, or about 2-30% by weight, or about 3-25% by weight or about 5-20% by weight, based on the total weight of the curable composition.

EXAMPLES

Example 1. Synthesis Using Diphenylmethanol as an Initiator Alcohol

The following generally describes processes to prepare a benzhydryl polyetheramine alkoxylate according to the present disclosure:

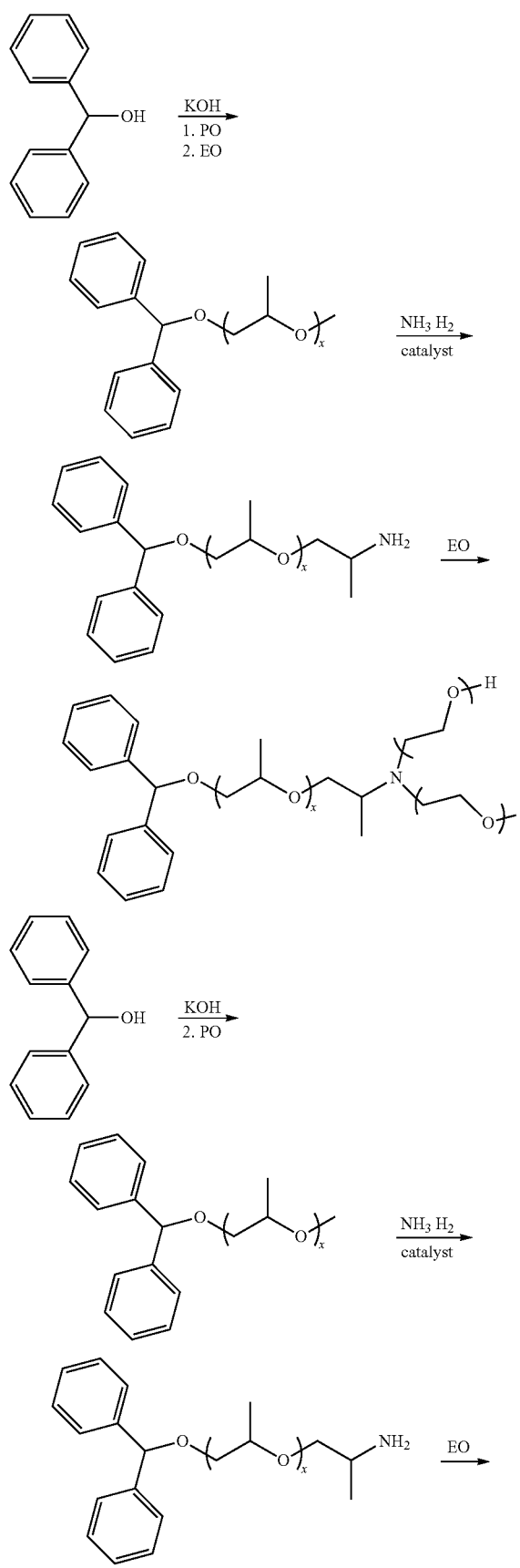

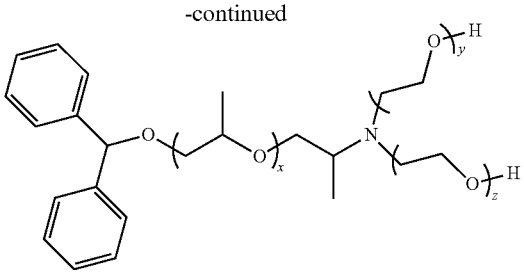

For example, propylene oxide was used to alkoxylate diphenylmethanol (x=about 4) and then ethylene oxide were used alkoxylate the polyetheramine (m+n=5).

More specifically, 3.5 lbs of benzhydrol and 50 g potassium methoxide were charged to a reactor and heated to 100° C. while applying vacuum to remove any water or methanol. The temperature was then increased to 125° C. and 4.4 lbs propylene oxide were added at a rate that maintained the temperature between 125°–135° C. When the propylene oxide addition was complete, the reaction was digested for 1 additional hour at 130° C., and finally the reaction was nitrogen stripped for 30 minutes to remove any unreacted propylene oxide. The benzhydrol propoxylate was then reductively aminated with $H_2$ and $NH_3$ in a continuous reactor at 190° C. with a heterogeneous catalyst to produce the amine. The amine (4.48 lbs) was charged to a reactor and heated to 120° C. and 0.95 lbs ethylene oxide was charged at a rate to keep the temperature between 145°–150° C. to ethoxylate the amine. Then, the reactor was cooled to 90° C. and 8 g KOH was added to the reaction and an additional 1.42 lbs ethylene oxide was reacted to bring the moles ethylene oxide per amine group to 5. The reaction was finally nitrogen stripped at 140° C. for 30 min. to remove any unreacted ethylene oxide to yield the benzhydryl polyetheramine ethoxylate as a yellow viscous liquid. This surfactant was added to a glyphosate-isopropylamine formulation at 10% (480 g/L glyphosate-IPA) and the resulting formulation was clear and flowable, and did not gel when added to water at the recommended use rate. Any foam formed in this dilution upon agitation quickly dissipated in 5 sec. or less, which is an advantage over the standard tallowamine ethoxylate adjuvant chemistry used for glyphosate which forms persistent foam upon agitation.

A series of 20 different benzhydryl etheramines and their ethoxylates were then made as above and evaluated in 480 g/L glyphosate-IPA formulations. Specifically, 1.5 g of the inventive compound was mixed with 10.0 g 62% IPA-glyphosate and 3.6 g deionized water to create the desired formulations. The cloud point of each formulation is shown below in Table 1.

TABLE 1

| moles PO before amination | EO moles post-amination (cloud point in ° C.) | | | | |
|---|---|---|---|---|---|
| | 2 | 5 | 10 | 15 | 20 |
| 2 | 96 | 74 | 73 | 52 | n/a |
| 3 | 100 | 98 | 79 | 63 | 32 |
| 4 | 100 | 93 | 79 | 64 | 42 |
| 6 | 73 | 80 | 74 | 64 | 48 |

As shown in Table 1, the inventive compounds can be used to formulate glyphosate concentrates that have high cloud points, which is important for storage stability.

Figure 2:
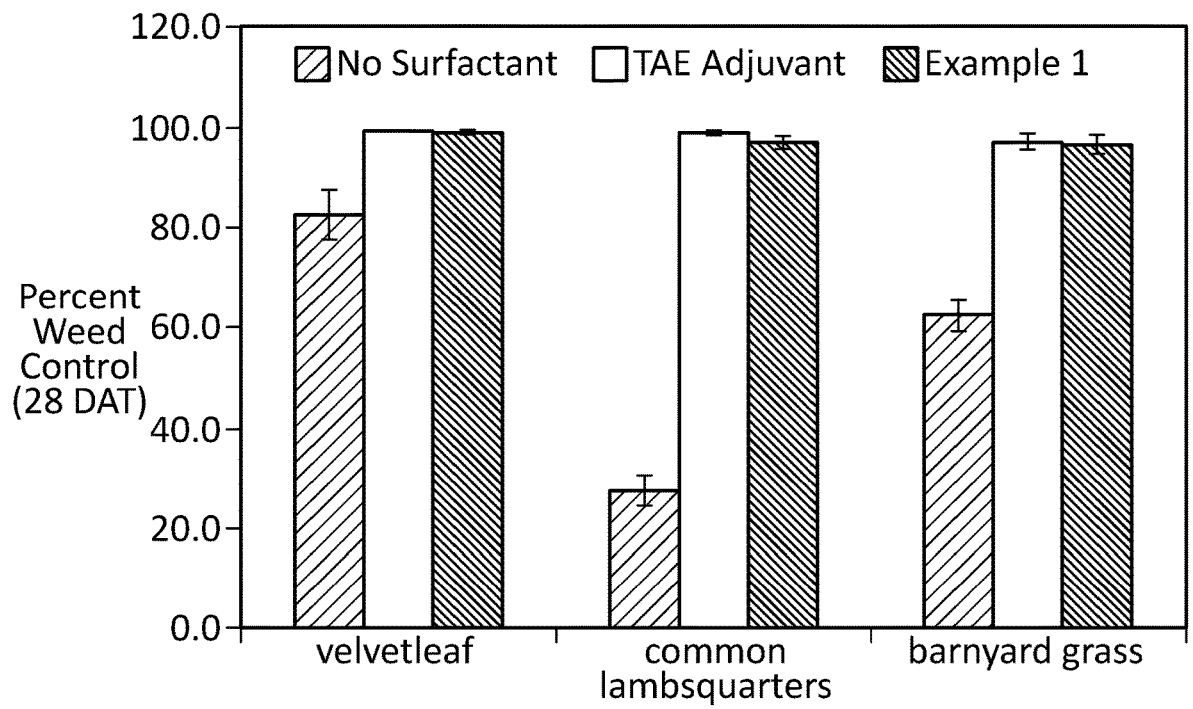

The benzhydryl polyetheramine alkoxylate initially prepared above was then evaluated as an adjuvant for enhancing the efficacy of glyphosate in a field trial. Tallow amine ethoxylates are the standard adjuvant used for glyphosate but are under regulatory pressure across their world for their perceived toxicity. In this trial, 0.5% w/w of each compound was added to a spray tank containing the recommended concentration of glyphosate. As shown in FIGS. 1 and 2, the inventive compound (Example 1) increases the weed-killing efficacy of glyphosate at least as well as the well-established tallow amine ethoxylate (TAE) chemistry.

Example 2. Betaine

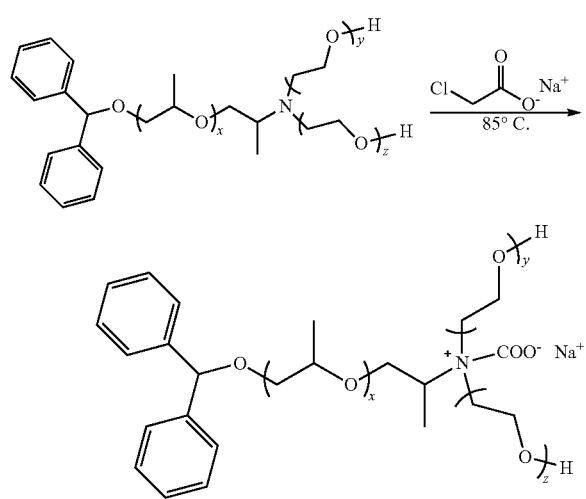

The benzhydryl etheramine ethoxylate from Example 1 was further reacted to create a betaine surfactant according to the above. 100.5 g of the amine (amine #1.49 meq/g) was mixed with 17.4 g sodium chloroacetate and 180 g $H_2O$ and the reaction was heated to 85° C. for 7 hours. The resulting product had an amine number of 0.36 meq/g, indicating that the amine was converted to the betaine at 75% conversion ratio. The betaine product was found to be soluble in water at neutral pH, whereas the parent amine was not. This surfactant was added to a glyphosate-isopropylamine formulation at 10% (480 g/L glyphosate-IPA) and the resulting formulation was clear and flowable, and did not gel when added to water at the recommended use rate.

Example 3. Phosphate Ester

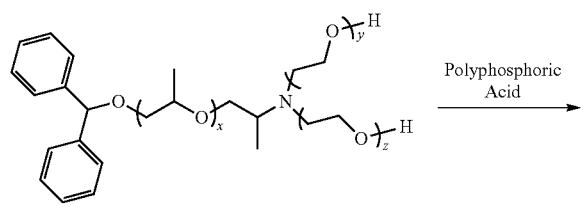

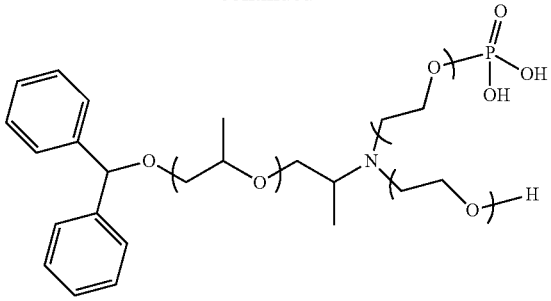

In this example (reaction scheme shown above), 94 g of the benzhydryl amine ethoxylate of Example 1 was reacted with 6 g polyphosphoric acid at 120° C. for 2 hours using a high shear rotor/stator mixer to generate the phosphate ester. The titration of the product showed one inflection point and the final acid number was measured at 75 mg/g KOH, which is near to the theoretical value of 77 mg/g KOH, showing efficient phosphation of the alcohol groups. This surfactant was added to a glyphosate-isopropylamine formulation at 10% (480 g/L glyphosate-IPA) and the resulting formulation was clear and flowable, and did not gel when added to water at the recommended use rate.

Example 4. N-Oxide

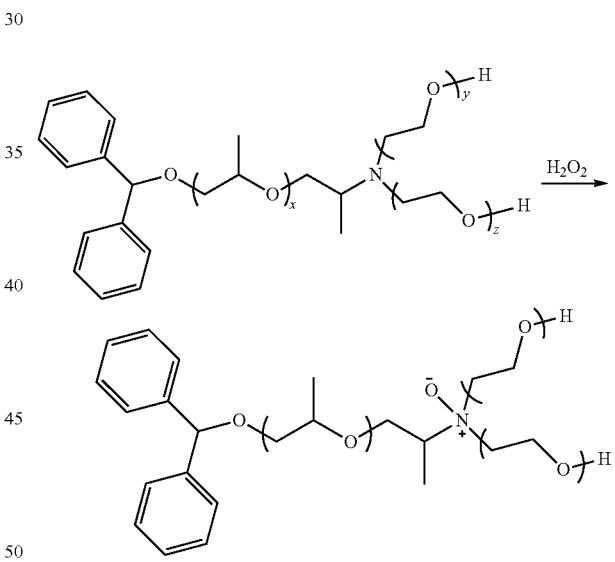

The benzhydryl etheramine ethoxylate from Example 1 was reacted further to synthesize an N-oxide surfactant according to the above. 100.5 g of the amine (amine #1.49 meq/g) was mixed with 180 g $H_2O$ and the reaction was heated to 60° C. and then 14.5 g 35% $H_2O_2$ was added for over 2 hrs. The reaction was heated further at 60° C. for 4 hours and the resulting product had an amine number of 0.26 meq/g, indicating that the amine was converted to the N-oxide at 83% conversion ratio. The N-oxide product was found to be soluble in water at neutral pH, whereas the parent amine was not. This surfactant was added to a glyphosate-isopropylamine formulation at 10% (480 g/L glyphosate-IPA) and the resulting formulation was clear and flowable, and did not gel when added to water at the recommended use rate.

While the foregoing is directed to various embodiments of the present disclosure, other and further embodiments of the disclosure may be devised without departing from the basic scope thereof, and the scope thereof is determined by the claims that follow.

The invention claimed is:

1. A polyetheramine alkoxylate compound having the formula (1)

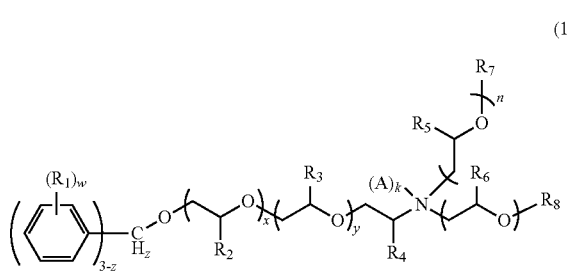

where $R_3$ and $R_4$ are each methyl; $R_5$, $R_6$, $R_7$, and $R_8$ are hydrogen; M is hydrogen, a water-soluble cation, a monovalent metal or a polyvalent metal cation; w is 0; z is 1; x is 0; y is an integer from 1 to 10; m is an integer from 0 to 50; n is an integer from 0 to 50; k is 0; and wherein m+n=1 to 10.

2. A method for preparing a polyetheramine alkoxylate compound having the formula (1) according to claim 1 comprising the steps of: reacting an initiator alcohol selected from phenylmethanol, diphenylmethanol, triphenylmethanol and a mixture thereof with ethylene oxide, propylene oxide, butylene oxide or mixture thereof to form a precursor polyol; aminating the precursor polyol to form a polyetheramine; and, alkoxylating the polyetheramine with an alkylene oxide to form the polyetheramine alkoxylate of formula (1).

3. The method of claim 2, wherein the method further comprises the step of reacting the polyetheramine alkoxylate compound of formula (1) with an acidic moiety and optionally neutralizing with a source of alkali metal, alkaline earth metal, amine or ammonia.

4. A composition comprising a polyetheramine alkoxylate compound having the formula (1)

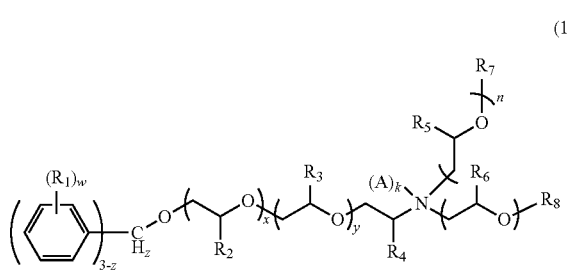

where $R_3$ and $R_4$ are each methyl; $R_5$, $R_6$, $R_7$ and $R_8$ are hydrogen; M is hydrogen, a water-soluble cation, a monovalent metal or a polyvalent metal cation; w is 0; z is 1; x is 0; y is an integer from 1 to 10; m is an integer from 0 to 50; n is an integer from 0 to 50; k is 0; and wherein m+n=1 to 10 and a solvent.

5. A packaged product comprising: a) a container having at least an outlet; and b) the composition of claim 4.

6. A concentrate composition comprising from about 50% by weight of the compound of the formula (1) according to claim 1 and from about 0.5% by weight to about 50% by weight of water and optionally one or more additives, where the % by weight is based on the total weight of the concentrate composition.

7. A performance chemical formulation or personal care formulation comprising the composition of claim 4, wherein the compound of formula (1) is present in an amount ranging from about 0.01% by weight to about 40% by weight, based on the total weight of the performance chemical formulation.

8. An agrochemical emulsifiable concentrate comprising an agrochemical active component, a solvent and the composition of claim 4 wherein the compound of formula (1) is present in an amount ranging from about 1% w/w to about 20% w/w, where w/w means the weight of the composition comprising the compound of formula (1) present in the agrochemical emulsifiable concentrate over the total weight of the agrochemical emulsifiable concentrate.

9. An agrochemical suspension concentrate comprising an agrochemical active component, water and the composition of claim 4 wherein the composition comprising the compound of formula (1) may be present in the agrochemical suspension concentrate in an amount ranging from about 0.01% w/w to about 10% w/w, where w/w means the weight of the composition comprising the compound of formula (1) present in the agrochemical suspension concentrate over the total weight of the agrochemical suspension concentrate.

10. An agrochemical soluble liquid concentrate comprising a dissolved agrochemical active ingredient, water, and the composition of claim 4 wherein the composition comprising the compound of formula (1) may be present in the agrochemical soluble liquid concentrate in an amount ranging from about 0.01% to about 20% w/w, where w/w means the weight of the composition comprising the compound of formula (1) present in the agrochemical soluble liquid concentrate over the total weight of the agrochemical soluble liquid concentrate.

11. A fuel additive concentrate comprising the composition of claim 4, one or more performance additives and at least one of a fuel, a carrier oil or a solvent.

12. A curable composition comprising the compound of formula (1) of claim 1 and a curable resin.

* * * * *